United States Patent
Corbett

(10) Patent No.: US 9,833,314 B2
(45) Date of Patent: Dec. 5, 2017

(54) PERCUTANEOUS VALVE DEPLOYMENT

(75) Inventor: Scott C. Corbett, Beverly, MA (US)

(73) Assignee: Abiomed, Inc., Danvers, MA (US)

(*) Notice: Subject to any disclaimer, the term of this patent is extended or adjusted under 35 U.S.C. 154(b) by 518 days.

(21) Appl. No.: 12/761,931

(22) Filed: Apr. 16, 2010

(65) Prior Publication Data

US 2011/0257739 A1    Oct. 20, 2011

(51) Int. Cl.
*A61F 2/82* (2013.01)
*A61F 2/24* (2006.01)

(52) U.S. Cl.
CPC .......... *A61F 2/2412* (2013.01); *A61F 2/2415* (2013.01); *A61F 2/2418* (2013.01); *Y10T 29/49826* (2015.01)

(58) Field of Classification Search
CPC ..................................... A61F 2/24; A61F 2/82
USPC ................................................. 623/2.18, 2.19
See application file for complete search history.

(56) References Cited

U.S. PATENT DOCUMENTS

| | | |
|---|---|---|
| 5,037,434 A | 8/1991 | Lane |
| 5,116,564 A | 5/1992 | Jansen et al. |
| 5,258,023 A | 11/1993 | Reger |
| 6,117,169 A | 9/2000 | Moe |
| 6,165,215 A | 12/2000 | Rottenberg et al. |
| 2003/0114924 A1 | 6/2003 | Moe |
| 2004/0024452 A1 | 2/2004 | Kruse et al. |
| 2004/0088046 A1* | 5/2004 | Speziali .................. 623/2.19 |
| 2009/0222082 A1 | 9/2009 | Lock et al. |

FOREIGN PATENT DOCUMENTS

| | | |
|---|---|---|
| JP | H02168961 | 6/1990 |
| WO | WO93/18721 | 9/1993 |
| WO | WO-98/32400 | 7/1998 |
| WO | WO98/51239 | 11/1998 |
| WO | WO-03/063740 | 8/2003 |
| WO | WO2007016251 | 2/2007 |
| WO | WO2007130537 | 12/2007 |

OTHER PUBLICATIONS

International Search Report for PCT/US2011/032560 dated Aug. 16, 2011.
Examination Report for Australian patent application No. 2011239561, dated Jan. 20, 2014.
International Search Report for international patent application No. PCT/US2011/032559, dated Jul. 9, 2011.

* cited by examiner

*Primary Examiner* — Matthew Schall
(74) *Attorney, Agent, or Firm* — White & Case LLP

(57) ABSTRACT

A polymeric heart valve is disclosed including: a valve body having a central axis having a body fluid pathway extending along the central axis from an inflow end to an outflow end; a flexible stent disposed about an outer circumference of the body and including at least three flexible stent posts each extending in the axial direction to a tip; and at least three flexible leaflets extending from the stent, each of the leaflets having an attached edge defining an attachment curve along the stent extending between a respective pair of stent posts.

39 Claims, 12 Drawing Sheets

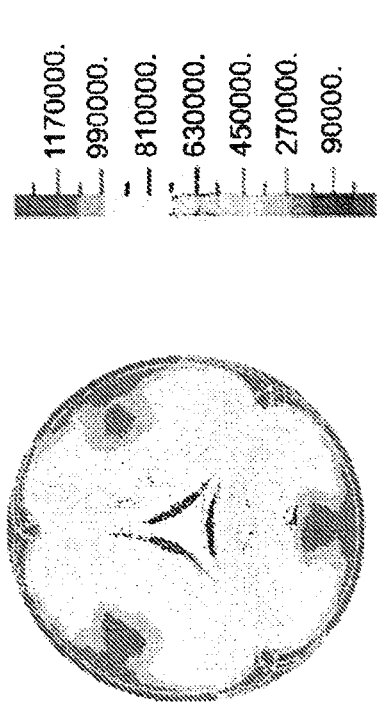
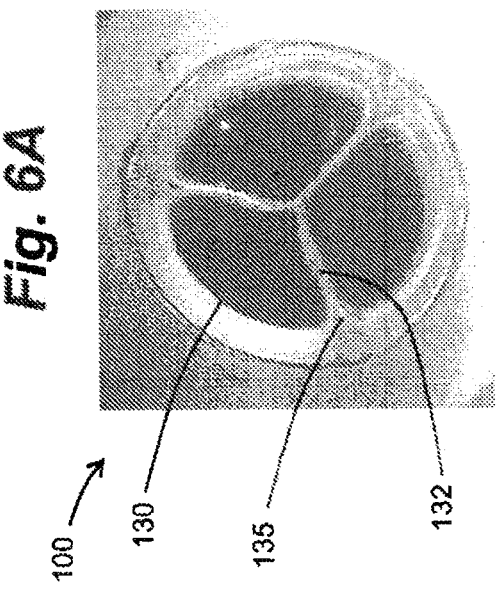
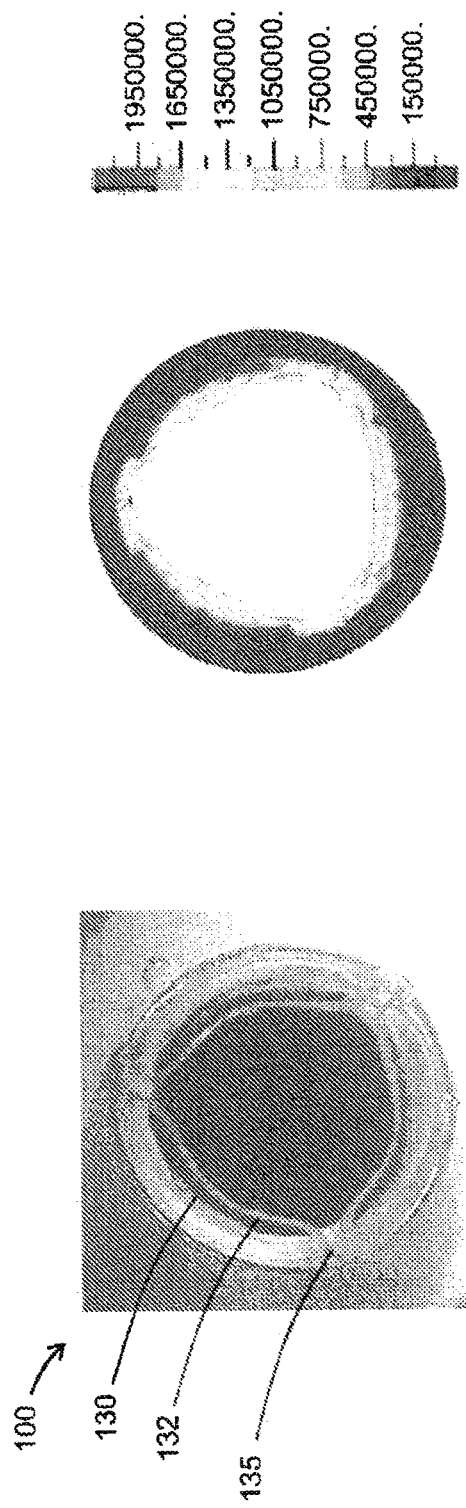
Fig. 6A
Fig. 6B
Fig. 7A
Fig. 7B

PERCUTANEOUS VALVE DEPLOYMENT

BACKGROUND

Prosthetic heart valves are used to replace damaged or diseased heart valves. Prosthetic heart valves for human patients have been available since the 1950s. Today, there are three general types of prosthetic heart valves, including mechanical valves, tissue valves, and polymer valves. A heart valve prosthesis is implanted into an annular opening in a patient's heart following surgical removal of a diseased or damaged natural valve. The valve can be secured in the annulus of the opening through the use of sutures or pins that penetrate the host tissue and an outside edge of the valve. Alternatively, the valve can be secured in the annulus by suturing the host tissue to a sewing ring. Heart valves function essentially as one-way check valves for blood flow through the beating heart.

The term "mechanical valve" refers to mono- or bi-leaflet heart valves having a valve orifice fabricated at least in part of a rigid, biologically compatible material such as pyrolytic carbon, and comprising essentially no biological components. The term "bioprosthetic valve" refers to a bi-leaflet or tri-leaflet heart valve having at least some biological components such as tissue or tissue components. The biological components of tissue valves are obtained from a donor animal (typically bovine or porcine), and the valve may comprise either biological materials alone or biological materials with man-made supports or stents. The term "polymeric valve" refers to a tri-leaflet or bi-leaflet heart valve having at least some elastomeric polymer components, including at least elastomeric polymer valve leaflets.

A tri-leaflet heart valve prosthesis typically includes an annular valve body and three flexible leaflets attached thereto. The valve body includes an annular base and three leaflet support posts, called a "stent," located at the circumference of the annulus. A sewing ring annularly coupled to the periphery of the valve body provides a place for sutures to be applied when the valve is implanted. The leaflets are attached to the three shaped posts along an attachment curve, and they also each have a free, unattached edge remote from the attachment curve. The place where two adjacent leaflets come together at one of the support posts of a stent is called the commissure, and the generally curved area on the leaflet between the free edge and the attachment curve is known as the belly of the leaflet. The free edges of the three leaflets come together at a "triple point" generally on the axis of the valve.

When blood flows in the forward direction, the energy of the blood flow deflects the three leaflets away from the center of the annulus and allows blood to flow through. When blood flows in the reverse direction, the three leaflets engage each other in a coaptive region, occlude the valve body annulus and prevent the flow of blood.

SUMMARY

In view of the above, existing prosthetic heart valves cannot be considered ideal for human patients. For example, bioprostheses valves suffer from durability problems requiring replacement, while mechanical valves require life-long anticoagulation. Although polymeric valves have the potential to address both of the shortcomings of the bioprostheses and mechanical valves, they have failed to satisfy durability, forward flow pressure loss and efficiency requirements.

The inventors have realized that a multi-leaflet polymeric heart valve (e.g. a tri-leaflet valve) may be provided with a partially open leaflet position which reduces forward flow pressure loss. The valve features a flexible stent having posts with tips made of a soft flexible material. The flexibility of the stent allows the leaflets to properly close to block reverse blood flow without experiences excessive stress or strain. These features act synergistically to provide a valve with advantageous durability, forward flow pressure loss and efficiency characteristics.

In one aspect, an exemplar polymeric heart valve is disclosed, including: a valve body having a central axis and having a body fluid pathway extending along the central axis from an inflow end to an outflow end; a flexible stent disposed about an outer circumference of the body and including at least three flexible stent posts each extending in the axial direction to a tip; and at least three flexible leaflets extending from the stent, each of the leaflets having an attached edge defining an attachment curve along the stent extending between a respective pair of stent posts, and where pairs of leaflets define a respective commissure at each of the at least three stent posts; where: the at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end, and in the closed position, each of the flexible stent posts flexes inward toward the central axis.

In some embodiments, the tip of each stent post is formed of a material having a flexibility greater than the remainder of the stent post.

In some embodiments, in the closed position, each flexible stent serves as a strain relief for a leaflet transition to the stent.

In some embodiments, each leaflet includes a free edge and a belly.

In some embodiments, for each respective leaflet, the free edge extends along a free edge curve between a respective pair of stent posts. And in the partially open position at rest, the portions of the free edge curve which are proximal the respective stent posts extend in the axial direction towards the outflow end of the valve body, such that the leaflet includes a homed portion proximal the stent posts.

In some embodiments, the tip of each flexible stent post extends beyond the free edge of the leaflets proximal the tip.

In some embodiments, the at least three leaflets open symmetrically in response to forward blood flow.

In some embodiments, in the open position, the blood flow velocity through each commissure is substantially the same as that blood flow velocity through the other commissures of the valve.

In some embodiments, the energy required to move the leaflets from the partially open position at rest to the open position during forward blood flow is less than the energy required to open the leaflets of an equivalent valve formed in a closed position at rest.

In some embodiments, the tip of each flexible stent post extends beyond the free edge of the leaflets proximal the tip.

In some embodiments, the tip of each flexible stent post extends beyond the free edge of the leaflets by about 1.5 mm.

In some embodiments, each flexible leaflet is made from a biocompatible polymer.

In some embodiments, the biocompatible polymer is selected from a group consisting of silicone and polyurethane.

In some embodiments, the belly of the leaflet has a thickness profile less than a thickness profile of the free edge of the leaflet.

In some embodiments, the partially open position at rest, the opening of the commissures at positions closest to their respective flexible stent post ranges between 0.1 mm and 0.6 mm.

In some embodiments, the opening is about 0.25 mm.

In some embodiments, the stent is made from a biocompatible polymer.

In some embodiments, the biocompatible polymer is selected from a group consisting of silicone and polyurethane.

In some embodiments, the tip of each flexible sent post is made from a biocompatible polymer.

In some embodiments, the biocompatible polymer is polyurethane.

Some embodiments include a sewing ring coupled to the valve body at a position axially distal to the flexible stent posts from the outflow end, the sewing ring providing a place for sutures to be applied when the valve is implanted.

In some embodiments, the sewing ring is snap fit into a groove in the valve body.

In some embodiments, in the closed position, reverse blood flows through an opening between each of the respect pairs of adjacent leaflets in an region proximal to the respective commissure to provide wash out of the commissure.

In another aspect, a method of making a polymeric heart valve is disclosed, including: providing a valve body having a central axis and having a body fluid pathway extending along the central axis from an inflow end to an outflow end; positioning a flexible stent about an outer circumference of the body, the stent including at least three flexible stent posts each extending in the axial direction; attaching flexible material to each stent of the at least three stent post to form a flexible tip on the respective stent post; and forming at least three flexible leaflets extending from the stent, each of the leaflets having an attached edge defining an attachment curve along the stent extending between a respective pair of stent posts, and where pairs of leaflets define a respective commissure at each of the at least three sent posts.

In some embodiments, the at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end, and in the closed position, each of the flexible stent posts flexes inward toward the central axis.

In some embodiments, the step of attaching flexible material includes adhering one or more strips of polymeric material to each of the stent posts.

In some embodiments, the one or more strips of polymeric material includes polyurethane.

In some embodiments, the step of forming at least three flexible leaflets includes: mounting the valve body and stent on a mandrel to form a mandrel assembly; and after the step of attaching flexible material, dip coating the mandrel assembly in a polymeric solution to form the leaflets.

Some embodiments include applying multiple dip coats of polymer solution to the mandrel assembly form the leaflets with a desired thickness profile.

In some embodiments, each leaflet includes a free edge and a belly.

In some embodiments, the belly of the leaflet has a thickness profile less than a thickness profile of the free edge of the leaflet.

In some embodiments, for each respective leaflet, the free edge extends along a free edge curve between a respective pair of stent posts; and in the partially open position at rest, the portions of the free edge curve which are proximal the respective stent posts extend in the axial direction towards the outflow end of the valve body, such that the leaflet includes a homed portion proximal the stent posts.

In some embodiments, the dip coating forms the leaflets attached to each other, and further including separating the leaflets to form the commissures and place the leaflets in the partially open position at rest.

In some embodiments, separating the leaflets includes laser cutting the leaflets to form a free edge on each leaflet.

In some embodiments, the partially open position at rest, the opening of the commissures at positions closest to their respective flexible stent post ranges between 0.1 mm and 0.6 mm.

In some embodiments, the opening is about 0.25 mm.

In some embodiments, the tip of each stent post is formed of a material having a flexibility greater than the remainder of the stent post.

In some embodiments, in the closed position, each flexible stent serves as a strain relief for a leaflet transition to the stent.

In some embodiments, the energy required to move the leaflets from the partially open position at rest to the open position during forward blood flow is less than the energy required to open the leaflets of an equivalent valve formed in a closed position at rest.

In some embodiments, at least one of the stent, the at least three leaflets, and the valve body is made from a biocompatible polymer.

In some embodiments, the biocompatible polymer is selected from a group consisting of silicone and polyurethane.

In another aspect, an exemplary polymeric heart valve made by a process including the steps of: providing a valve body having a central axis and having a body fluid pathway extending along the central axis from an inflow end to an outflow end; positioning a flexible stent about an outer circumference of the body, the stent including at least three flexible stent posts each extending in the axial direction; attaching flexible material to each stent of the at least three stent post to form a flexible tip on the respective stent post; and forming at least three flexible leaflets extending from the stent, each of the leaflets having an attached edge defining an attachment curve along the stent extending between a respective pair of stent posts, and where pairs of leaflets define a respective commissure at each of the at least three sent posts.

In some embodiments, the at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end, and in the closed position, each of the flexible stent posts flexes inward toward the central axis.

Various embodiments may include any of the above described features, alone, or in any suitable combination.

The present embodiments provide at least the following advantages over prior art prosthetic heart valves. First, a flexible stent allows the normally partially open leaflets to properly close and reduces stress concentrations in the leaflets thereby decreasing forward flow pressure loss and increasing reliability due to leaflet tears. Second, the flexible stent post effectively transfers force from the leaflets to stent without high stress concentrations providing greater reliability. Third, the normally partially open leaflets improve the valve kinematics, e.g., by reducing or eliminating the incidence of a "lazy leaflet" (i.e., a leaflet that does not properly move during opening or closing of the valve) and as such reducing the valves tendency to produce thrombosis.

These advantages allow for the utilization of thinner leaflets that yield better performance with respect to forward flow pressure loss, while increasing reliability.

BRIEF DESCRIPTION OF THE DRAWINGS

FIGS. 5A, 5C, 5E, and 5G show a side view of the stent post;

FIGS. 5B, 5D, 5F, and 5H show a front view of the surface of the stent post facing toward the central axis of the valve.

FIGS. 6A and 6B show views of a polymeric valve in the open position and the closed position, respectively.

FIGS. 7A and 7B show finite element analysis stress plots corresponding to the valve positions shown in FIGS. 6A and 6B, respectively.

DETAILED DESCRIPTION

Generally, the present technology relates to polymeric heart valves that increase valve reliability and reduce forward flow pressure loss. The polymeric heart valve includes a body, a flexible stent including at least three flexible stent posts, and at least three flexible leaflets. The valve leaflets are cast in a partially open position at rest requiring the stent posts to flex or deflect towards the center of the valve body in order for the leaflets to fully close.

Figure 1:
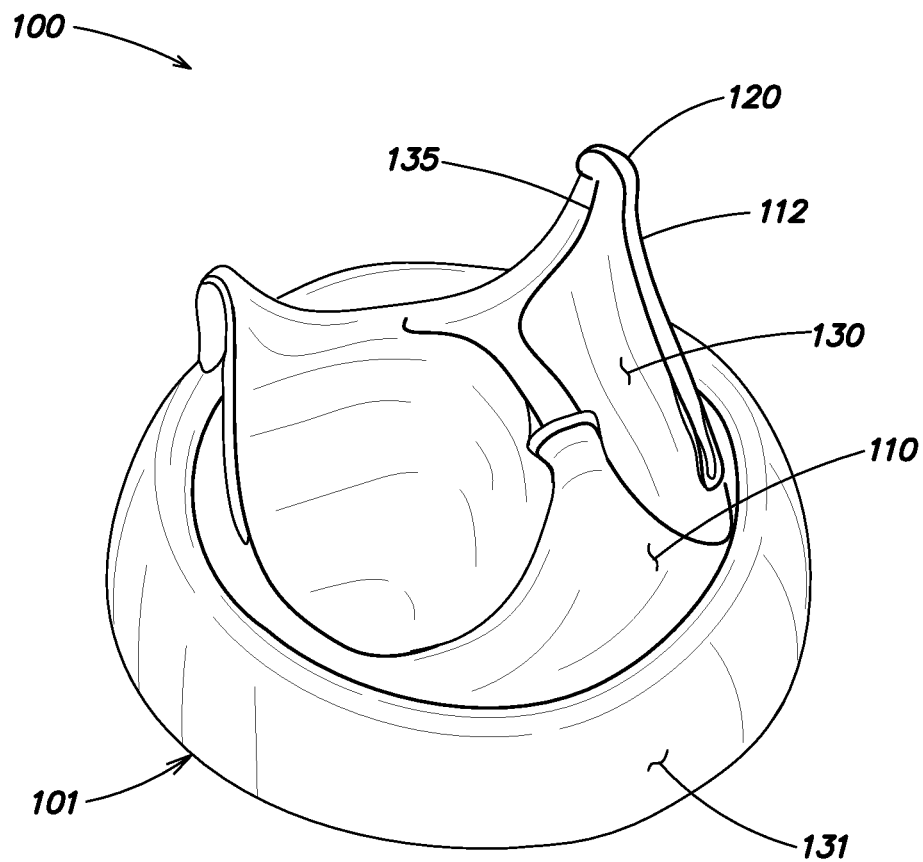
FIG. 1 shows a photograph of one embodiment of a polymeric heart valve.
Figure 1A:
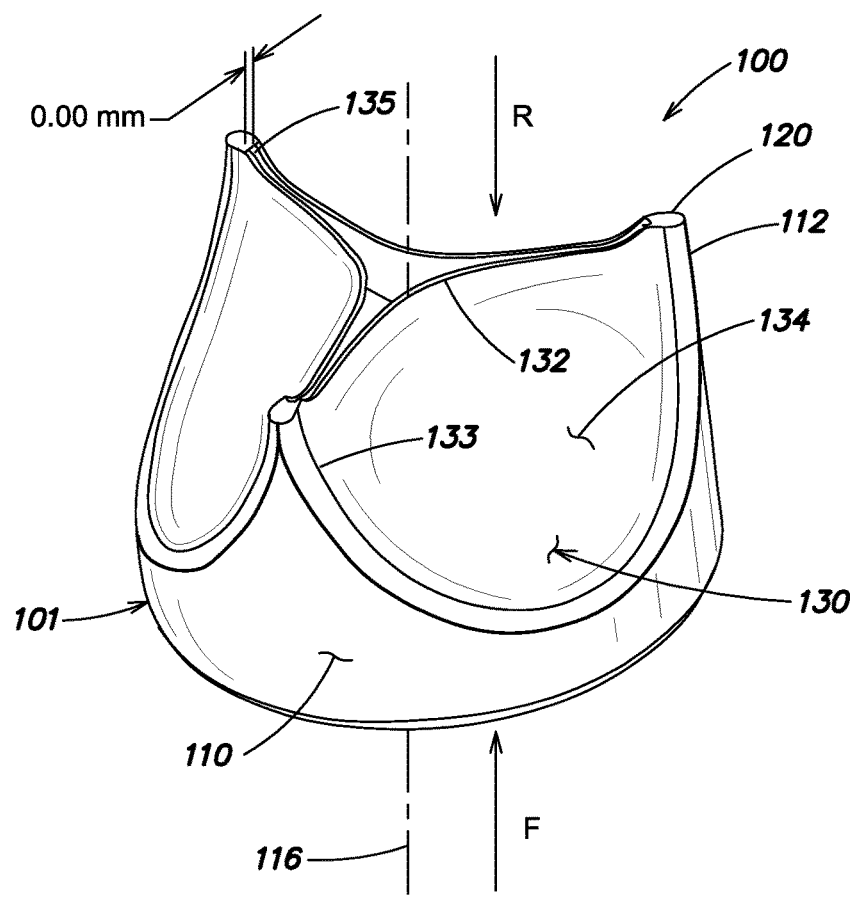
FIG. 1A shows a perspective view of the polymeric heart valve of FIG. 1.
Figure 1B:
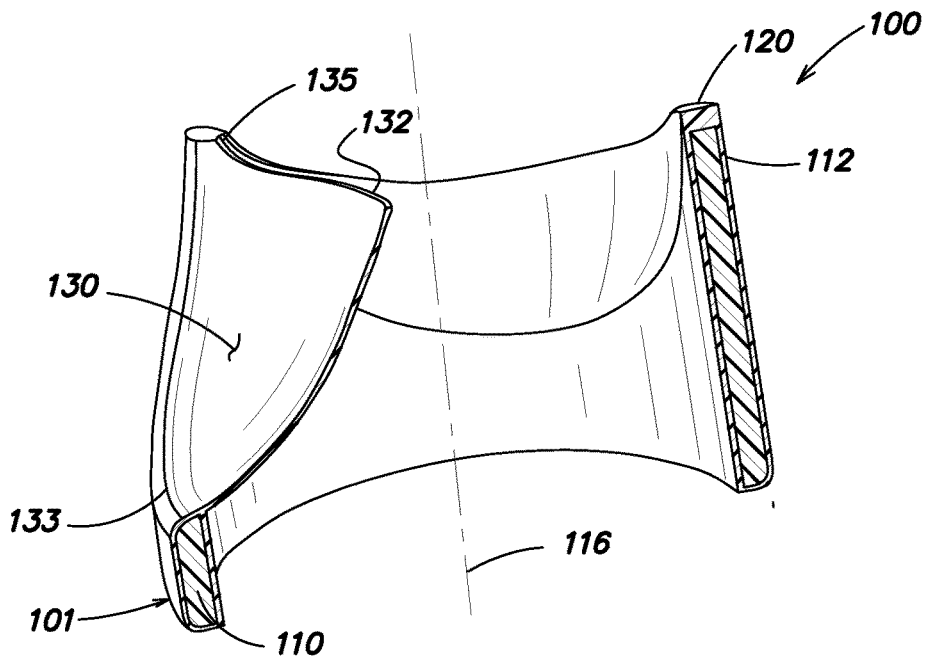
FIG. 1B is a cross-sectional view of the polymeric heart valve of FIG. 1A.

FIGS. 1, 1A and 1B show one embodiment of a polymeric heart valve 100. The heart valve 100 includes an annular, generally cylindrical elastomeric valve body 101 disposed about a central axis 116, and having a sealable fluid passageway extending axially from an inflow end (as shown, the bottom) to an outflow end (as shown, the top). The valve 100 includes a flexible stent 110 having at least three flexible stent posts 112 each of which extends axially to a stent post tip 120. As discussed in greater detail below, stent post tip 120 may be made of a material having greater flexibility than the stent post 112. The valve 100 may also include a sewing ring 131 (not shown in FIGS. 1A and 1B).

The valve includes at least three flexible leaflets 130 each having a free edge 132, and attached edge 133 and a belly 134. The attached edge 133 attaches to stent 110 to form an attachment curve running along the inner diameter of the stent between a pair of stent posts 112. The free edge 132 defines a free edge curve which extends from a first stent post tip 120, towards the central axis 116 and back to second stent post tip 120. The free edges 132 of adjacent leaflets 130 define commissures 135 at each of the stent post tips 120. In some embodiments, the free edges 132 curve upward in the region of the commissures 135, such that the leaflets 130 have a horned shape in the region around each of the stent post tips 120, as shown.

In operation, when blood flows in the forward direction, i.e., in the direction of the arrow F shown in FIG. 1A, the pressure of the blood flow causes the leaflets 130 to deflect away from a central axis 116 of the valve body 101. In this "open" position, the leaflets 130 define a large flow orifice (not shown) allowing the blood to flow freely in the forward direction. With the leaflets 130 in the open position, the valve 100 presents little resistance to fluid flow. When blood flows in the reverse direction, i.e., in the direction of the arrow R shown in FIG. 1A, the pressure of the blood flow causes the stents 120 and the leaflets 130 to deflect toward the central axis 116. In this "closed" position, the leaflets 130 engage each other along the free edges 132, which help the valve 100 seal against reverse flow.

As shown, the leaflets 130 are cast in a partially open position at rest (i.e. in the absence of forward or reverse fluid pressure against the valve). For example, in some embodiments the at rest opening of commissures in the region closest to their respective flexible stent post tip 120 is in the range of 0.60 mm or less, e.g. about 0.25 mm.

For example, the open area of the valve in the at rest position (e.g., the open cross sectional area presented to fluid flow through the valve) may be a suitable fraction of the open area of the valve in the absence of the leaflets 130. In some embodiments the open area in the partially open at rest positions may be greater than 5%, 10%, 25% or more of the open area, e.g., in the range of 5-10%, 10-20%, 10-30%, or any other suitable range.

This configuration reduces the energy required to open the leaflets during forward blood flow relative to that required to open an equivalent valve which is formed in a closed position at rest. The relative ease of opening of valve 100 when formed in the partially open rest position results in a decrease in forward flow pressure loss.

Furthermore, the partially open rest position leaflet geometry helps ensure a symmetric opening of the leaflets 130 in response to forward flow, even in cases where the flow is not uniformly distributed (e.g. due to the specifics of the heart anatomy, or other factors). For example, by providing the leaflets 130 in the partially open rest configuration, the valve can avoid unwanted adhesion of free edges of one or more pairs of adjacent leaflets 130 to one another. This prevents low fluid velocities in the commissure 135 between the leaflets 130.

Moreover, this valve structure can reduce or prevent the occurrence a "lazy leaflet", i.e., a leaflet that does not properly and complexly move between its intended open and closes positions.

Avoiding low fluid flow and/or asymmetric flow patterns allows the valve to be properly washed through by the flow of blood in both forward and reverse directions, reducing or eliminating the build up of unwanted materials in the valve. This can lead to a reduction or even elimination of deleterious effects, e.g., thrombosis.

When transitioning from the partially open rest position to the closed position, stent posts 112 flex inward toward the central axis to allow leaflets 130 to close properly to seal the valve against reverse flow. This flexing beneficially reduces strain on the leaflets 130, reducing or eliminating the occurrence of tears, and improving the reliability and durability of valve 100. Moreover, in some embodiments, the tips 120 of stent posts are formed of a material which is more flexible than the remainder of the stent posts 120. This allows for increased flexing in the area near the commissures 135 without compromising the overall structural integrity of posts 120. Accordingly, force may be transferred from the leaflets 130 to the stent posts 112 through tips 120 while reducing or eliminating unwanted stress concentrations in the leaflets 130. In other words, the flexible stent post tips 120 serve as a strain relief for the leaflet 130 transition to the stent posts 112 while reducing stress concentrations in the leaflets 130 thereby increasing reliability of the polymeric valve 100. Note also that, due to the transition from stiff to soft material in the stent posts 120, relatively short, low profile posts 120 may be used.

As shown in FIGS. 1A and 1B, each flexible stent post tip 120 extends beyond the free edge 132 of the leaflets 130 where the leaflets attach to the posts 112 (i.e. near commissures 135). In some embodiment, each flexible stent tip 120 extends beyond the free edge of the leaflets by 1 mm to 2 mm, e.g., by 1.5 mm. In some embodiments, This flexible stent tip configuration acts to reduces stress concentrations between the softer leaflet 130 material and the harder stent post 112 in order to increase the valve reliability.

As shown in FIGS. 1A and 1B, a portion of the free edge 132 of the leaflet 130 is substantially straight, extending radially towards the central axis 116. As noted above, in one embodiment, portions of the free edge 132 of the leaflet 130 curve upward slightly at the stent post tip 120 tip. In one embodiment, the belly 134 of the leaflet 130 has a thickness profile less than a thickness profile of the free edge 132 of the leaflet 130. The thickness profile of the free edge 132 can be in the range of 1 to 2.5 times greater than the thickness profile of the belly 134. The leaflets can be made from a biocompatible polymer, such as silicone and/or polyurethane.

Figure 2:
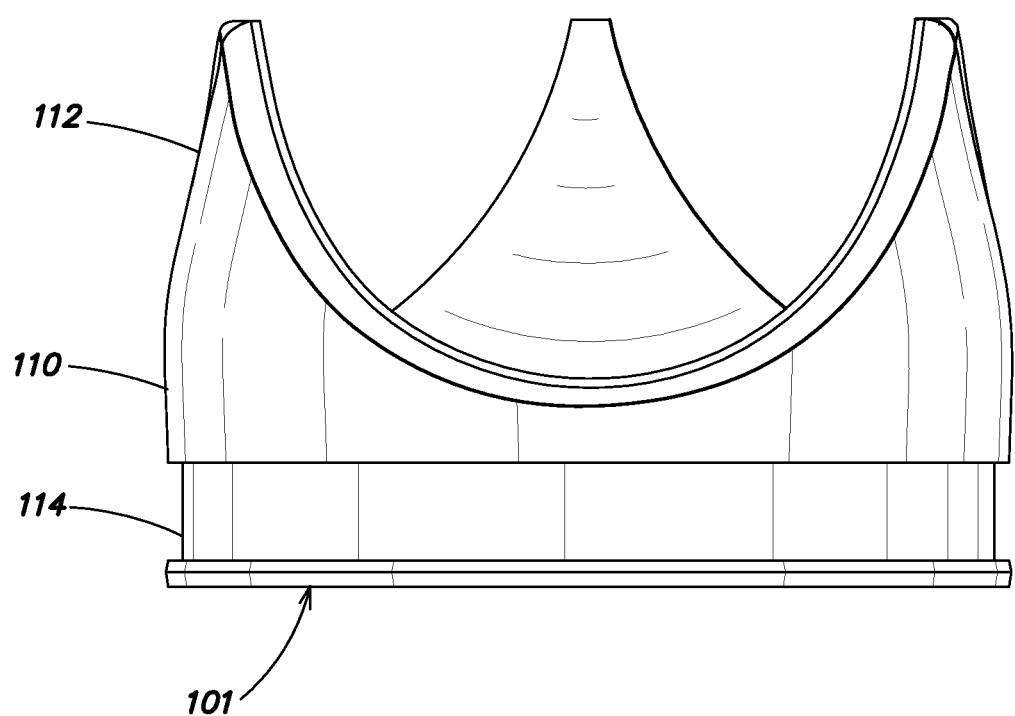
FIG. 2 shows the body of a polymeric heart valve including a stent.
Figure 2A:
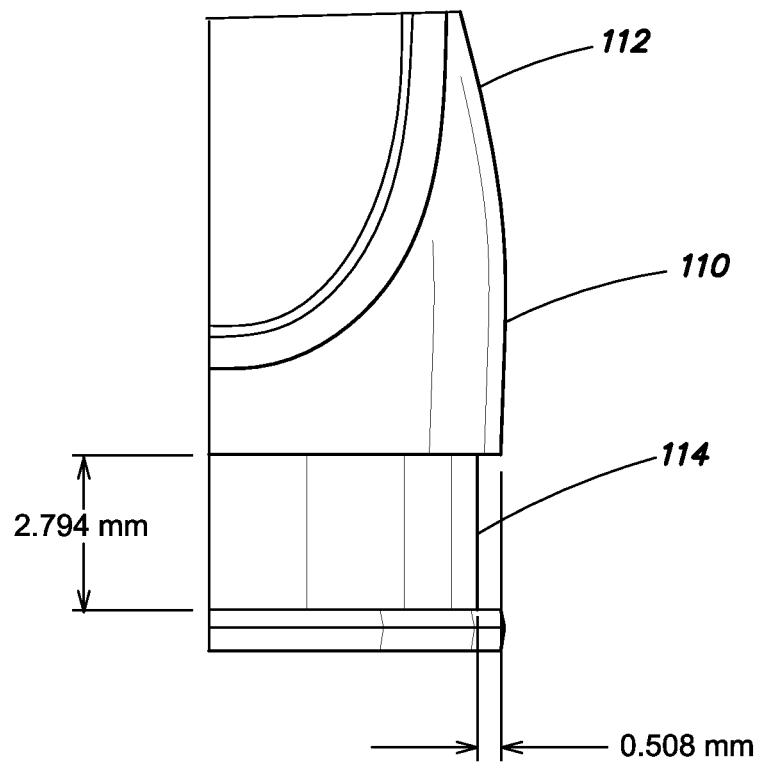
FIG. 2A shows an embodiment of a groove on the body of a polymeric heart valve to accept a sewing cuff.

As shown in FIGS. 2 and 2A, the stent 110 is disposed about the outer diameter of the valve body 101. The stent 110 includes at least three protrusions which form posts 112, the protrusions having a thickness extending in the radial direction (i.e. perpendicular with respect to the central axis 116). The body 101 includes and a groove 114 running circumferentially about the body 101 in a direction transverse to the central axis 116. The groove 114 is for accepting a sewing ring that provides a place for sutures to be applied when the valve is implanted. In one embodiment, the valve body 101 is made from a biocompatible polymer, such as silicone, polyurethane, polyether ether ketone (PEEK), etc. In some embodiments, the valve body 101 defines a central opening of in the range of about 10 mm to about 30 mm, e.g., 21.4 mm and a thickness in the range of about 0.5 mm to about 2 mm, e.g. 1.25 mm. In some embodiments, The protrusions extending from the valve body have length in the range of about 5 mm to about 20 mm, e.g., 11.0 mm measured from the base of the valve body 101 and a thickness of in the range of about 0.5 to about 2 mm, e.g., 1.25 mm. In some embodiments, the grove 114 has a height in the range of about 1 mm to about 5 mm, e.g., 2.8 mm and a depth in the range of about 0.1 mm to about 1 mm, e.g., 0.5 mm. It should be understood that the valve body 101 and stent 110 can be dimensioned in multiple configurations.

Figure 2B:
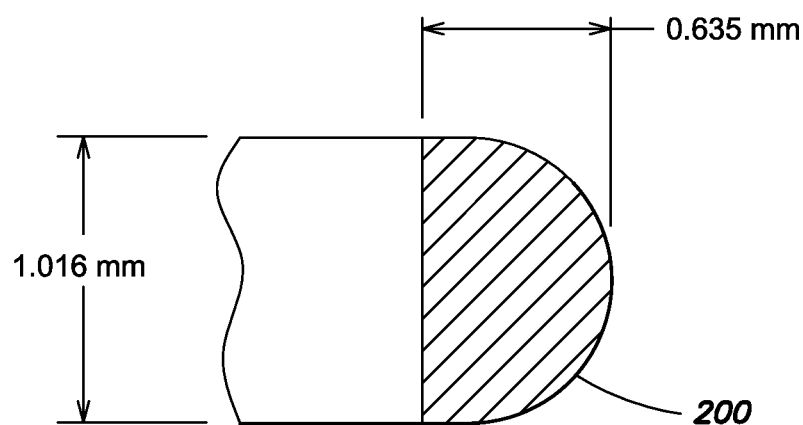
FIG. 2B is a cross-sectional view of a stainless steel ring for securing the sewing cuff in the groove of FIG. 2A.

FIG. 2B is a cross-sectional view of a stainless steel ring 200 for securing the sewing cuff in the grove 114 of FIG. 2A. In one embodiment, the stainless steel ring 200 has a height of 1.0 mm and a width of 0.64 mm; and an inner diameter (I.D.) of 24.4 mm and an outer diameter (O.D.) of 25.8 mm. In one embodiment, the sewing ring is made from approximately 38.1 mm of Meadox® tubular double velour. The tubular double velour can be purchased from Meadox Medicals, Inc., 112 Bauer Drive, Oakland, N.J.

Figure 3:
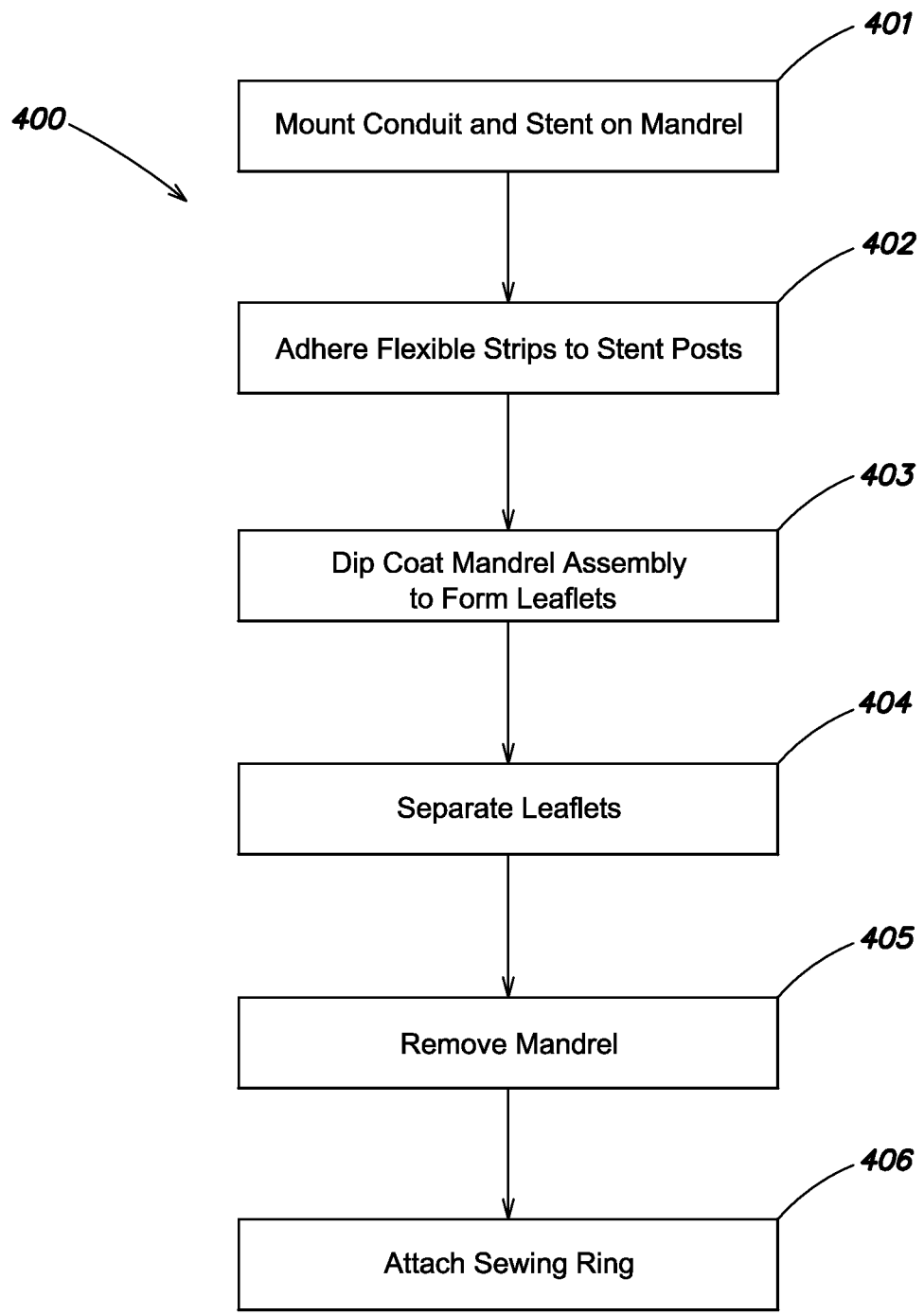
FIG. 3 is a flow chart for a process for fabricating a polymeric heart valve.

Referring to FIG. 3, in some embodiments, the steps of process 400 can be followed to produce the polymeric heart valve 100 (e.g. as shown in FIGS. 1-1B), however it should be understood that different variations and combinations of these steps could be used.

In step 401, a polymer conduit 310 and stent 110 are mounted on a mandrel 300. Referring to FIG. 3, first, the valve mandrel 300 is prepared for accepting the valve body 110. For example, the valve mandrel 300 and the stent 110 should be cleaned with alcohol. Next, a polymer conduit 310 is placed on the valve mandrel 300 and the stent 110 is placed on the polymer conduit 310 over the valve mandrel 300. The polymer conduit 310 should extend from the bottom of the stent 110, e.g., by about 1 mm. Further, the stent posts 112 of the stent 110 should line up with the cusps 302 of the valve mandrel 300. At this point, any residual portion of conduit 310 should be removed at the edges of the cusps 302. Additionally, the conduit may be cut to length or otherwise removed to provide a stand alone valve 100.

In step 401, strips of flexible material are adhered to stent posts 112 to form the basis of stent tips 120. In one embodiment, a first set of three polymeric strips are cut from a polymeric sheet, each having a dimension of about 1-1.3 mm×3 mm×5 mm. In one embodiment, the polymeric sheet can be Angioflex produced by Abiomed of Danvers, Mass. Next, a second set of three polymeric strips are cut from the residual conduit, each having a dimension of about 0.15-0.25 mm×3 mm×10 mm.

Figure 5A:
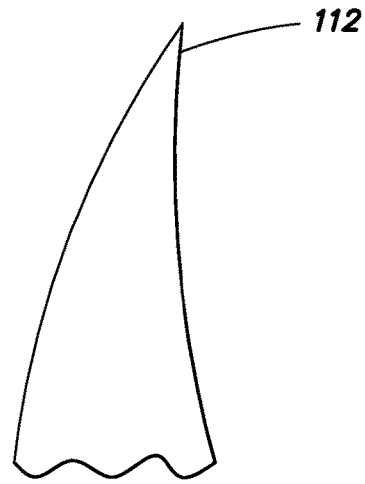
FIGS. 5A-5H illustrate the formation of a flexible stent tip on a stent post of a polymeric heart valve.
Figure 5B:
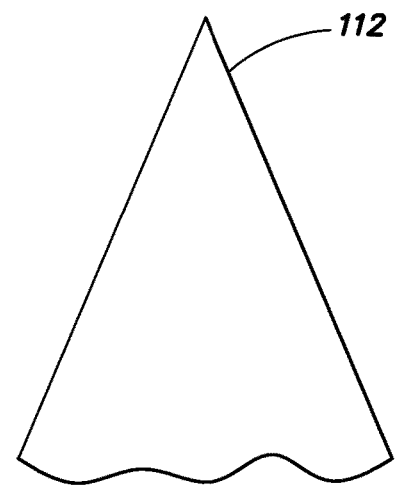
Figure 5C:
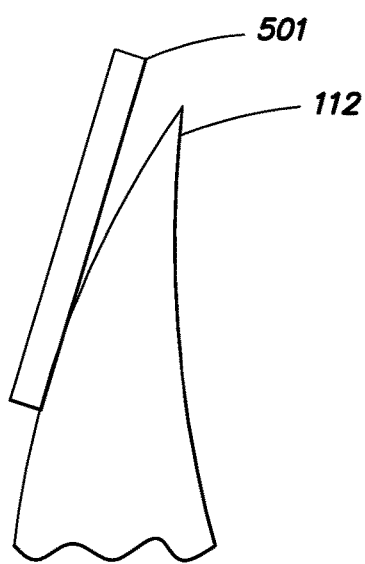
Figure 5D:
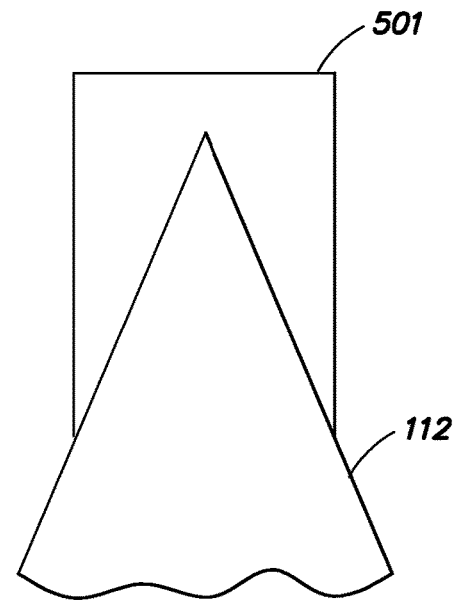
Figure 5E:
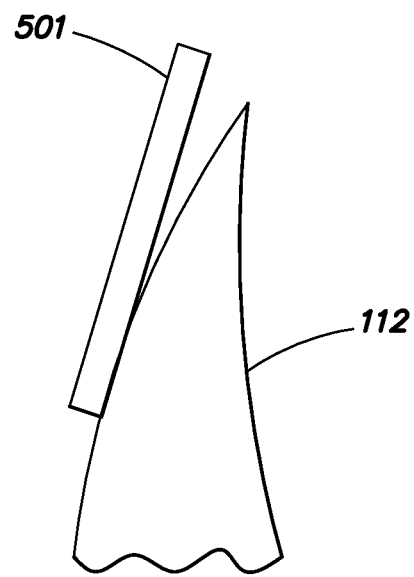
Figure 5F:
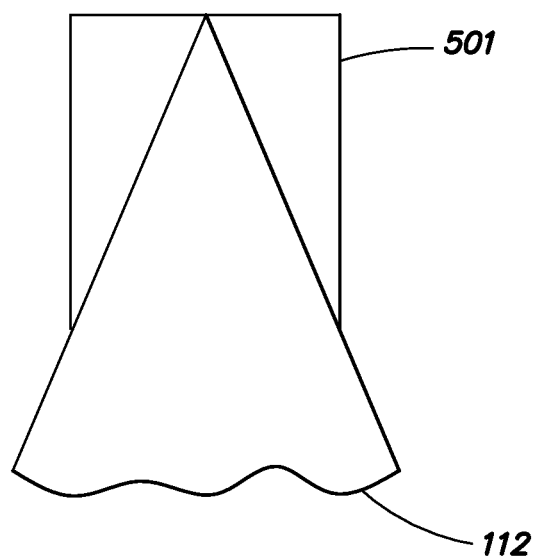

FIGS. 5A and 5B show the end of a stent post 112 prior to application of the strips. The first set of strips 501 are adhered to the posts 112 using a UV cure epoxy. In one embodiment, the recommended exposure time is approximately 3.5 seconds. FIGS. 5C and 5D show. Next, the second set of strips (not shown) are adhered to the adjoining line of the protrusions 112 and the first set of strips using the UV cure epoxy. In one embodiment, the recommended exposure time is approximately 4.5 seconds. In other embodiments the strips may be adhered using other suitable techniques, e.g., using a solvent based method. Referring to FIGS. 5E and 5F, the strips 501 are trimmed so that they are even with the protrusion 112 tips.

Figure 4:
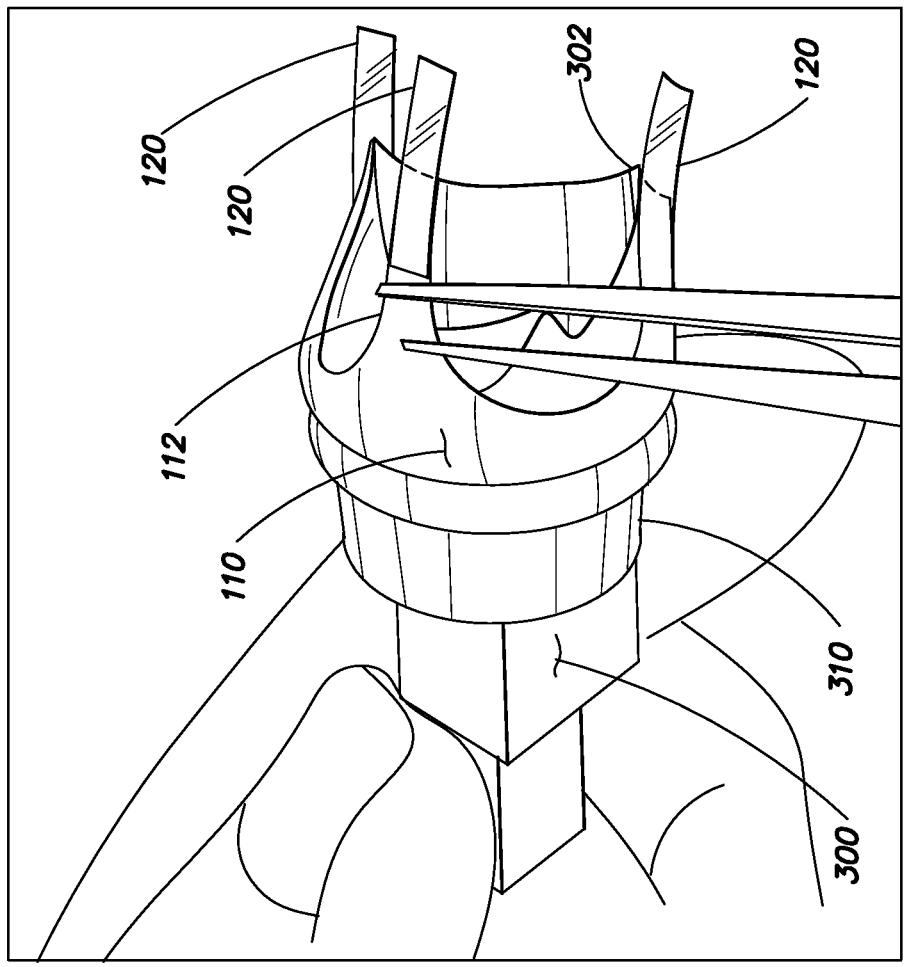
FIG. 4 is a view of a polymeric heart valve being assembled on a dip coating mandrel.

Referring back to FIGS. 3 and 4, in step 403, the prepared valve mandrel 300 assembly, including conduit 310 and stent 110 (now with strips 501 attached to its stent posts 120), is dip coated to form leaflets 130. The mandrel assembly is dipped in a polymer solution having a suitable viscosity, e.g., within the 730±50 cp range. In some embodiments, the polymer solution can be an Angioflex solution produced by Abiomed of Danvers, Mass. At this step, the valve mandrel 300 is cleaned, e.g. with alcohol. Next, the valve mandrel 300 is placed upside down in a container of Dioxane, e.g., for 30 seconds so that the entire stent 110 is covered. Next, the valve mandrel 300 is dipped in the polymer solution, e.g., such that all of the stent 110 is dipped in the polymer solution. Once the valve mandrel 300 is removed from the solution it is spun on a rotator for 20-30 minutes to remove any excess solution. The dipping process may be repeated to obtain a desired leaflet 130 profile. In one embodiment, the dipping process is repeated, for a total number of six dips, where each stent post 112 enters the solution twice. After the last dip, the mandrel is spun on the rotator, e.g., for approximately 12 hours. Next, the valve mandrel 300 is placed in an oven, e.g., for approximately one hour. In one embodiment, the oven is set to about 100° C. The valve mandrel 300 is removed from the oven and cooled at room temperature, e.g., for approximately two hours. Next, the cured polymeric solution may be trimmed, e.g., off the mandrel flats as desired (e.g. using scissors, or a hot wire, or other trimming techniques known in the art).

Figure 5G:
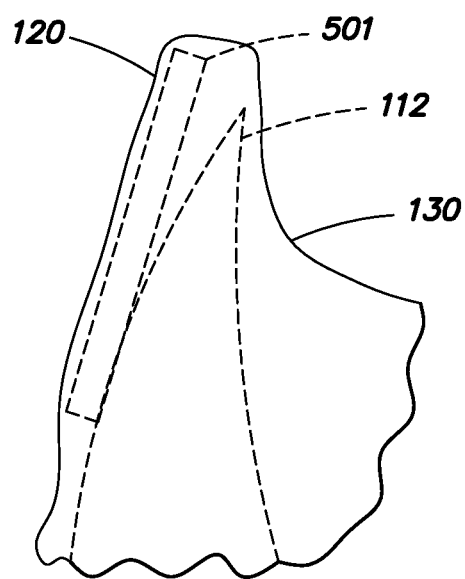
Figure 5H:
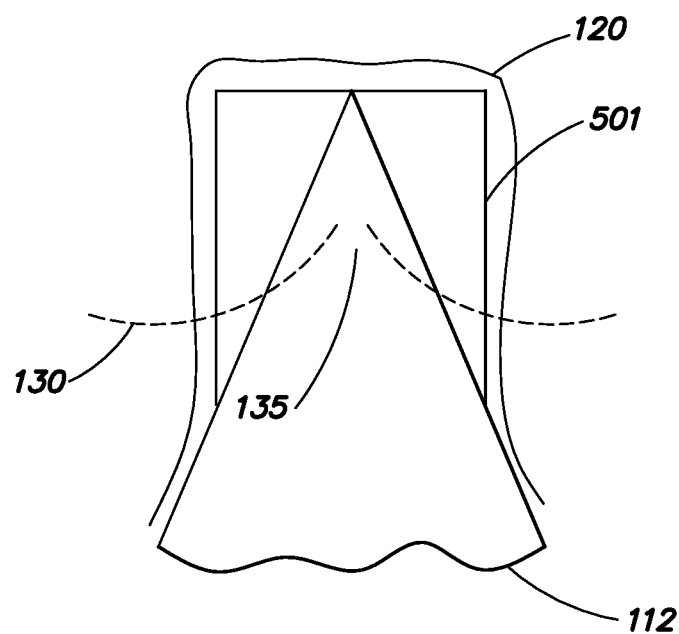

Referring to FIGS. 5G and 5H, following the dipping process, the stent post tips 120 have been formed around strips 501 on the ends of stent posts 112. The leaflets 130 have been formed, but are currently in an attached configuration, with no free edges.

In step 404, the leaflets are separated. With reference to FIG. 1A, in one embodiment, each free edge 132 of the leaflet 130 is laser cut to provide a highly uniform edge, e.g., with the substantially portions described above. In one embodiment, portions of the free edge 132 of the leaflet are laser cut to curve upward slightly at the stent 120 tip.

In step 405, the valve 100 is removed from the mandrel 300. In some embodiments, the valve mandrel is placed in a water bath, e.g., for about one hour. In one embodiment, the water temperature is set to about 37° C. Following the water bath, the valve 100 is removed from the mandrel 300. Leaflets 130 are now in the partially open position at rest, as described in detail above.

In step 406, sewing ring 131 is attached to the valve 100. To create the sewing ring for the valve 100 (FIG. 1), the tubular velour is placed around the O.D. of the valve body 110 and centered around the axis of the groove 114 in an axial direction. Next, as shown in FIG. 2B, the stainless steel ring 200 is snap-fitted into the groove 100 which restricts movement of the tubular velour. Lastly, the velour is folded over the stainless steel ring 200 until both ends meet and the ends are stitched together to create the sewing ring. Optionally, the velour can be folded and stitched multiple times to increase the thickness of the sewing ring. In one embodiment, a polymeric material can be placed between the sewing ring and the valve body 101 as to further secure the sewing ring to the valve 100. The polymeric material can be a biocompatible polymer such as silicone or polyurethane.

Although one valve fabrication process has been described above, it is to be understood that any suitable fabrication technique know in the art may be employed. For example, the valve 100 may be fabricated using one or more of the techniques described in Labma N M K, Woodhouse K A, Cooper S L. *Polyurethanes in Biomedical Applications.* 1998 CRC Press LLC, Boca Raton, Fla., p. 33.; Lyman D J, Searl W J, Albo D, Bergman S, Lamb J, Metcalf L C, and Richards K. Polyurethane elastomers in surgery. *Int J Polym Mater,* 5:211, 1977; Boretos J W. *Procedures for the fabrication of segmented polyurethane polymers into useful biomedical prostheses*. National Institutes of Health, 1968.; snf Kardos J L, Mehta B S, Apostolou S F, Thies C, and Clark R E. Design, fabrication and testing of prosthetic blood vessels. *Biomater Med Dev Artif Organs,* 2:387, 1974.

In general, valves described herein provide a number of advantages. As discussed above, the flexible stent tips operate to improve valve kinematics and reliability by reducing or eliminating undesirable stress or strain concentrations which might damage the thin leaflets 130, e.g., resulting in tears in sensitive areas, such as in the vicinity of commissures 135. FIGS. 6A and 6B show an embodiments of valve 100 in a fully open and a fully closed position, respectively. FIGS. 7A and 7B show finite element analysis stress plots corresponding to the valve positions shown in FIGS. 6A and 6B, respectively.

Referring to FIGS. 6A and 7A, note the full and symmetric opening of the leaflets 130 in the fully open position of valve 100 (with no "lazy leaflets"), allowing for proper wash through and reducing or eliminating the occurrence of thrombosis. Note also uniform distribution of stress across the leaflets 130, and the relatively modest stress concentrations in the vicinity of commissures 135.

Referring to FIGS. 6B and 7B, note the small openings between leaflets 130 in the vicinity of commissures 135. This configuration allows for proper wash through of the commissures during reverse flow, without undue reverse flow leakage or closing volume (as detailed below). Note also uniform distribution of stress across the leaflets 130, and the relatively modest stress concentrations in the vicinity of commissures 135 and along the free edges 132 of the leaflets 130. This stress profile advantageously reduces or eliminates tearing and wear.

Figure 8:
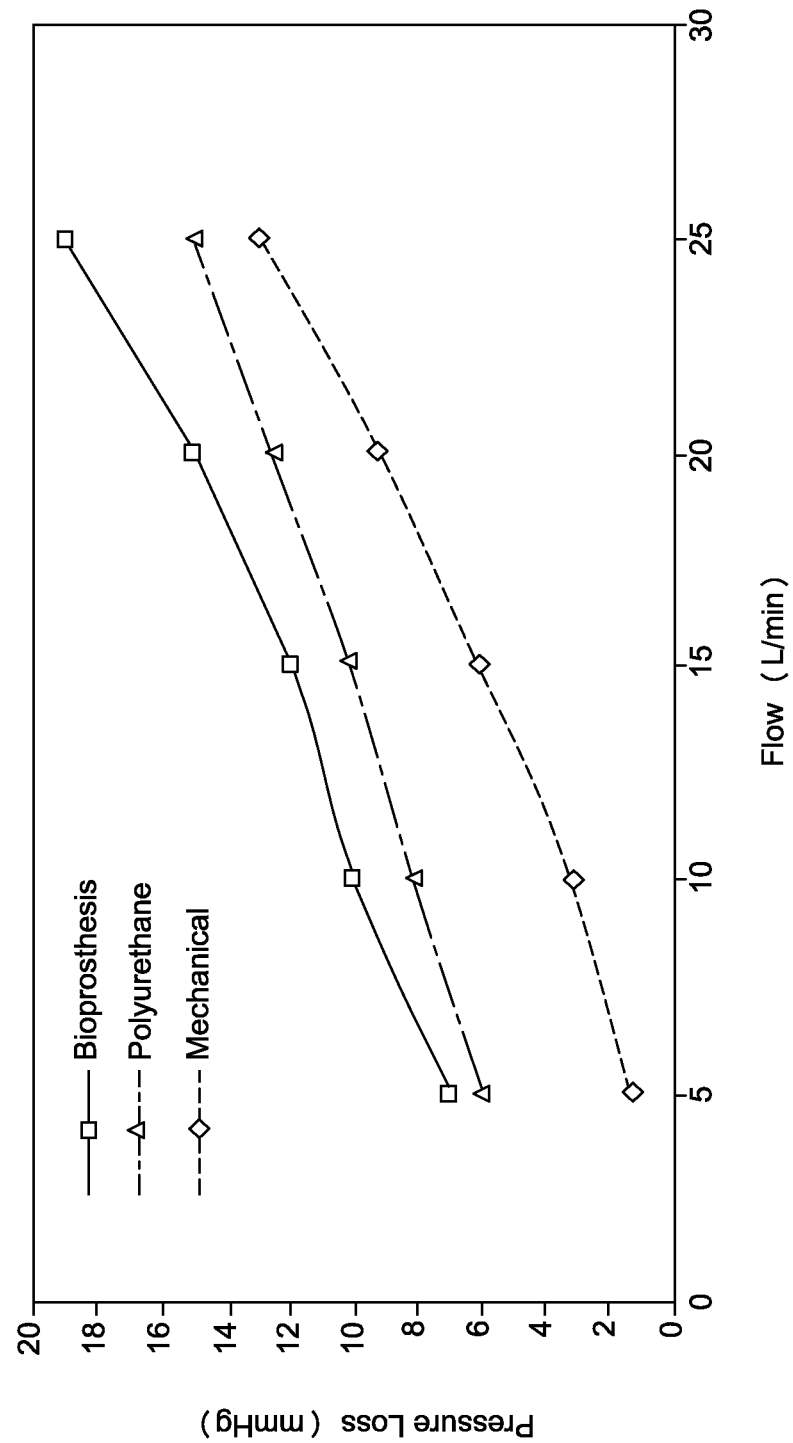
FIG. 8 shows a plot of forward pressure loss as a function of flow for a polymeric heart valve in comparison to similar plots for a mechanical valve and a bioprosthesis valve.

The valve 100, formed in the partially open position, may exhibit advantageous hemodynamic performance. FIG. 8 shows a plot of forward pressure loss as a function of flow rate for an embodiment of valve 100 constructed from polyurethane. The pressure loss increases roughly linearly as a function of flow rate, from a loss of about 6 mmHg at a flow rate of 5 L/minute to a loss of about 14 mmHg at a flow rate of 25 L/minute. Other embodiments may exhibit even lower pressure drops.

As shown, this performance is superior to that of a comparable bioprosthetic valve, and slightly diminished from that of a comparable mechanical valve. In many cases, the slightly increased pressure drop relative to a mechanical valve is more than offset by the utilization of flexible and peripherally located leaflets which avoid blood flow disturbances such as cavitation and stagnation leading to cell damage and thrombosis. Additional performance benefits include the avoidance of reliability issues typically associated with bioprosthesis (i.e., problems with limited life from structural changes such as calcification and leaflet wear, leading to valve failure—biological tissue fixation and methods used to mount the tissue to a supporting stent may account for this shortcoming).

Figure 9:
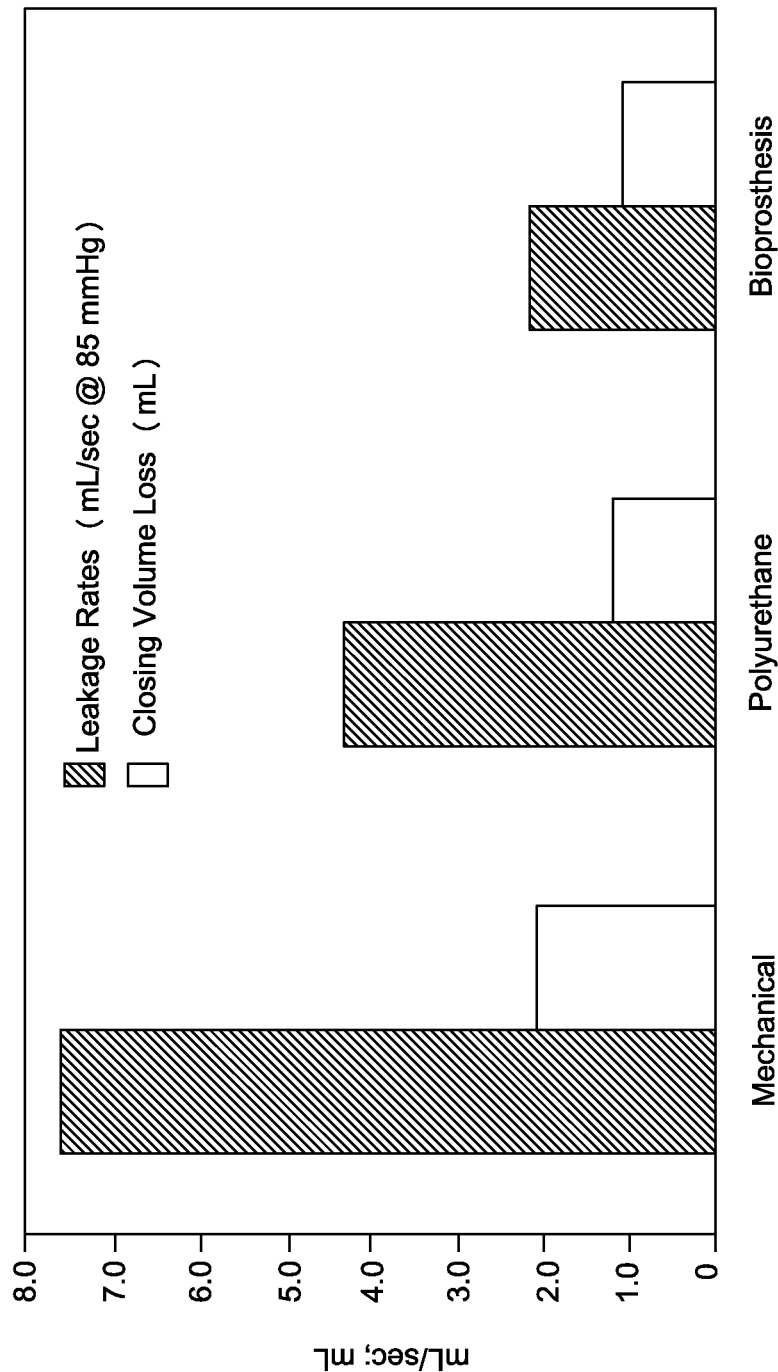
FIG. 9 shows a plot of leakage rate and closing volume for a polymeric heart valve in comparison to similar plots for a mechanical valve and a bioprosthesis valve.

FIG. 9 shows a plot of valve leakage and closing volume for an embodiment of valve 100 constructed from polyurethane. The valve leakage rate at a reverse flow pressure of 85 mmHg is less than about 4 mL/second. The closing volume loss of the valve is less than about 1 mL. As shown, this performance is superior to that of a comparable mechanical valve, and only slightly diminished from that of a comparable bioprosthesis valve.

The embodiments disclosed herein are to be considered in all respects as illustrative, and not restrictive of the invention. The technology described herein is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A polymeric heart valve, comprising:
   a valve body having a central axis and having a body fluid pathway extending along the central axis from an inflow end to an outflow end;
   a flexible stent supporting the body and comprising at least three flexible stent posts each extending in the axial direction to a tip, the tip of each stent post formed of a material adhered to a remainder of the stent post and having a flexibility greater than the remainder of the stent post; and
   at least three flexible leaflets extending from the stent, each of the leaflets having an attached edge defining an attachment curve along the stent extending between a respective pair of stent posts, wherein pairs of leaflets define a respective commissure at each of the at least three stent posts, and wherein the at least three leaflets and the tip of each of the at least three stent posts are integrally formed at the same time by dip coating the stent;
   wherein:
   the at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end, and
   in the closed position, each of the flexible stent posts flexes inward toward the central axis.

2. The polymeric heart valve of claim 1, wherein, in the closed position, each flexible stent serves as a strain relief for a leaflet transition to the stent.

3. The polymeric heart valve of claim 2, wherein each leaflet comprises a free edge and a belly.

4. The polymeric heart valve of claim 3, wherein:
   for each respective leaflet, the free edge extends along a free edge curve between a respective pair of stent posts; and
   in the partially open position at rest, the portions of the free edge curve which are proximal the respective stent posts extend in the axial direction towards the outflow end of the valve body, such that the leaflet includes a horned portion proximal the stent posts.

5. The polymeric heart valve of claim 4, wherein the tip of each flexible stent post extends beyond the free edge of the leaflets proximal the tip.

6. The polymeric heart valve of claim 3, wherein the at least three leaflets open symmetrically in response to forward blood flow.

7. The polymeric heart valve of claim 3, wherein, in the open position, the blood flow velocity through each commissure is substantially the same as that blood flow velocity through the other commissures of the valve.

8. The polymeric heart valve of claim 3, wherein the energy required to move the leaflets from the partially open position at rest to the open position during forward blood flow is less than the energy required to open the leaflets of an equivalent valve formed in a closed position at rest.

9. The polymeric heart valve of claim 3, wherein the tip of each flexible stent post extends beyond the free edge of the leaflets proximal the tip.

10. The polymeric heart valve of claim 9, wherein the tip of each flexible stent post extends beyond the free edge of the leaflets by about 1.5 mm.

11. The polymeric heart valve of claim 1, wherein each flexible leaflet is made from a biocompatible polymer.

12. The polymeric heart valve of claim 11, wherein the biocompatible polymer is selected from a group consisting of silicone and polyurethane.

13. The polymeric heart valve of claim 3, wherein the belly of the leaflet has a thickness profile less than a thickness profile of the free edge of the leaflet.

14. The polymeric heart valve of claim 1, wherein, in the partially open position at rest, the opening of the commissures at positions closest to their respective flexible stent post ranges between 0.1 mm and 0.6 mm.

15. The polymeric heart valve of claim 14, wherein the opening is about 0.25 mm.

16. The polymeric heart valve of claim 1, wherein the stent is made from a biocompatible polymer.

17. The polymeric heart valve of claim 16, wherein the biocompatible polymer is selected from a group consisting of silicone and polyurethane.

18. The polymeric heart valve of claim 1, wherein the tip of each flexible sent post is made from a biocompatible polymer.

19. The polymeric heart valve of claim 18, wherein the biocompatible polymer is polyurethane.

20. The polymeric heart valve of claim 1, further comprising a sewing ring coupled to the valve body at a position axially distal to the flexible stent posts from the outflow end, the sewing ring providing a place for sutures to be applied when the valve is implanted.

21. The polymeric heart valve of claim 1, wherein the sewing ring is snap fit into a groove in the valve body.

22. The polymeric heart valve of claim 1, wherein, in the closed position, reverse blood flows through an opening between each of the respect pairs of adjacent leaflets in an region proximal to the respective commissure to provide wash out of the commissure.

23. A method of making a polymeric heart valve, comprising:
   providing a valve body having a central axis and having a body fluid pathway extending along the central axis from an inflow end to an outflow end;
   positioning a flexible stent about an outer circumference of the body , the stent comprising at least three flexible stent posts each extending in the axial direction;
   attaching flexible material to each stent of the at least three stent posts to form a flexible tip on the respective stent post, the flexible material having a flexibility greater than the remainder of the stent post; and
   forming at least three flexible leaflets extending from the stent, each of the leaflets having an attached edge defining an attachment curve along the stent extending between a respective pair of stent posts, wherein pairs of leaflets define a respective commissure sure at each of the at least three sent posts, and wherein the at least three leaflets and the tip of each of the at least three stent posts are integrally formed at the same time by dip coating the stent;
   wherein:
   the at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end, and
   in the closed position, each of the flexible stent posts flexes inward toward the central axis.

24. The method of claim 23, wherein the step of attaching flexible material comprises adhering one or more strips of polymeric material to each of the stent posts.

25. The method of claim 24, wherein the one or more strips of polymeric material comprises polyurethane.

26. The method of claim 24, wherein the step of forming at least three flexible leaflets comprises:
mounting the valve body and stent on a mandrel to form a mandrel assembly; and
after the step of attaching flexible material, dip coating the mandrel assembly in a polymeric solution to form the leaflets.

27. The method of claim 26, comprising:
applying multiple dip coats of polymer solution to the mandrel assembly form the leaflets with a desired thickness profile.

28. The method of claim 25, wherein each leaflet comprises a free edge and a belly.

29. The method of claim 28, wherein the belly of the leaflet has a thickness profile less than a thickness profile of the free edge of the leaflet.

30. The method of claim 19, wherein:
for each respective leaflet, the free edge extends along a free edge curve between a respective pair of stent posts; and
in the partially open position at rest, the portions of the free edge curve which are proximal the respective stent posts extend in the axial direction towards the outflow end of the valve body, such that the leaflet includes a horned portion proximal the stent posts.

31. The method of claim 26, wherein the dip coating forms the leaflets attached to each other, and further comprising separating the leaflets to form the commissures and place the leaflets in the partially open position at rest.

32. The method of claim 31, wherein separating the leaflets comprises laser cutting the leaflets to form a free edge on each leaflet.

33. The method of claim 31, wherein, in the partially open position at rest, the opening of the commissures at positions closest to their respective flexible stent post ranges between 0.1 mm and 0.6 mm.

34. The method of claim 33, wherein the opening is about 0.25 mm.

35. The method of claim 23, wherein, in the closed position, each flexible stent serves as a strain relief for a leaflet transition to the stent.

36. The method of claim 23, wherein the energy required to move the leaflets from the partially open position at rest to the open position during forward blood flow is less than the energy required to open the leaflets of an equivalent valve formed in a closed position at rest.

37. The method of claim 23, wherein at least one of the stent, the at least three leaflets, and the valve body is made from a biocompatible polymer.

38. The method of claim 37, wherein the biocompatible polymer is selected from a group consisting of silicone and polyurethane.

39. A polymeric heart valve made by a process comprising the steps of:
providing a valve body having a central axis and having a body fluid pathway extending along the central axis from an inflow end to an outflow end;
positioning a flexible stent supporting the body, the stent comprising at least three flexible stent posts each extending in the axial direction;
attaching flexible material to each stent of the at least three stent post to form a flexible tip on the respective stent post, the flexible tip of each stent post having a flexibility greater than the remainder of the stent post; and
forming at least three flexible leaflets extending from the stent, each of the leaflets having an attached edge defining an attachment curve along the stent extending between a respective pair of stent posts, wherein pairs of leaflets define a respective commissure at each of the at least three sent posts, and wherein the at least three leaflets and the tip of each of the at least three stent posts are integrally formed at the same time by dip coating the stent;
wherein:
the at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end, and
in the closed position, each of the flexible stent posts flexes inward toward the central axis.

* * * * *

UNITED STATES PATENT AND TRADEMARK OFFICE
CERTIFICATE OF CORRECTION

PATENT NO. : 9,833,314 B2
APPLICATION NO. : 12/761931
DATED : December 5, 2017
INVENTOR(S) : Scott C. Corbett Page 1 of 1

It is certified that error appears in the above-identified patent and that said Letters Patent is hereby corrected as shown below:

In the Claims

In Claim 23, Column 12, Line number 53, please replace "of leaflets define a respective commissure sure at each" with -- of leaflets define a respective commissure at each --

In Claim 23, Column 12, Line number 54, please replace "of the at least three sent posts, and wherein the at least" with -- of the at least three stent posts, and wherein the at least --

Signed and Sealed this
Thirteenth Day of March, 2018

Andrei Iancu
*Director of the United States Patent and Trademark Office*